(12) United States Patent
DeRose et al.

(10) Patent No.: US 6,465,719 B1
(45) Date of Patent: Oct. 15, 2002

(54) CHIMERIC GENE ENCODING DROSOMYCIN, VECTOR CONTAINING IT AND PRODUCTION OF DISEASE-RESISTANT TRANSGENIC PLANTS

(75) Inventors: Richard DeRose, Lyons; Georges Freyssinet, Saint Cry au Mont d'Or; Jules Hoffman, Strasbourg, all of (FR)

(73) Assignee: Aventis Cropscience S.A., Lyon Cedex (FR)

( * ) Notice: Subject to any disclaimer, the term of this patent is extended or adjusted under 35 U.S.C. 154(b) by 0 days.

(21) Appl. No.: 09/480,251

(22) Filed: Jan. 11, 2000

Related U.S. Application Data

(63) Continuation of application No. PCT/FR98/01462, filed on Jul. 8, 1998.

(30) Foreign Application Priority Data

| Jul. 11, 1997 | (FR) | 97 09115 |
| Jul. 24, 1997 | (FR) | 97 09663 |

(51) Int. Cl.[7] ............ A01H 5/00; A01H 5/10; C12N 5/14; C12N 15/12; C12N 15/82
(52) U.S. Cl. ............ 800/301; 47/58.1; 435/320.1; 435/419; 536/23.5; 800/279
(58) Field of Search ............ 435/69.1, 420.1, 435/419, 468; 536/23.5; 800/278, 279, 298, 301; 47/58.1

(56) References Cited

U.S. PATENT DOCUMENTS 5,390,926 A   3/1994   Scheidegger et al. ...... 536/23.2

FOREIGN PATENT DOCUMENTS

| EP | 0507698 | 10/1992 |
| EP | 0508909 | 10/1992 |
| FR | 2725992 | 4/1996 |
| WO | 9119738 | 12/1991 |
| WO | 9319188 | 9/1993 |
| WO | 9514098 | 5/1995 |
| WO | 9603522 | 2/1996 |

OTHER PUBLICATIONS

Hartman, P.E. et al., (1960), J. Gen. Microbiol. 22:323.
Shedlovsky and Magasanik, (1962), J. Biol. Chem. 237:3725.
Shedlovsky and Magasanik, (1962), J. Biol. Chem. 237:3731.
Galloway and Taylor, (1980), J. Bacteriol. 144:1068.
Shioi et al., (1982), J. Biol. Chem., 257:7969.
Burton, (1955), Biochem. J. 61:473.
Burton, (1957), Biochem. J. 66:488.
Stougaard and Kennedy, (1988), J. Bacteriol., 170:250.
Johnson and Taylor, (1993) Applied Environ. Microbiol., 59:3509.
Proc. Natl. Acad. Sci., 88(10), pp. 4133–4137, (1991).
Lee et al., "Structure and Expression of Ubiquitin Genes of *Drosophila melanogaster*", *Molecular and Cellular Biology*, Nov. 1988, pp. 4727–4735.
Fehlbaum et al., "Insect Immunity, Septic Injury of Drosophilia Induces the Synthesis of a Potent Antifungal Peptide with Sequence Homology to Plant Antifungal Peptides", *J. Biol. Chem.*, vol. 269, No. 52, Dec. 30, 1994, pp. 33159–33163.

*Primary Examiner*—Amy J. Nelson
(74) *Attorney, Agent, or Firm*—Baker Botts LLP

(57) ABSTRACT

The invention concerns a chimeric gene containing a DNA sequence coding for drosomycin, a vector containing the chimeric gene, a method for transforming plants and the resulting transformed plants. The drosomycin produced by the plants provides them with resistance to diseases, in particular of fungal origin.

26 Claims, 2 Drawing Sheets

SEQUENCE LISTING

```
<160> NUMBER OF SEQ ID NOS:   15

<210> SEQ ID NO 1
<211> LENGTH: 488
<212> TYPE: DNA
<213> ORGANISM: Drosophila melanogaster
<220> FEATURE:
<221> NAME/KEY: CDS
<222> LOCATION: (101)...(310)

<400> SEQUENCE: 1
gaattcgagc tcggtacccc tcgagaccat ggtcgacccc acgcgtccgg ataattcttt      60
cagaaatcat ttaccaagct ccgtgagaac cttttccaat atg atg cag atc aag     115
                                              Met Met Gln Ile Lys
                                                1               5 tac ttg ttc gcc ctc ttc gct gtc ctg atg ctg gtg gtg ctg gga gcc     163
Tyr Leu Phe Ala Leu Phe Ala Val Leu Met Leu Val Val Leu Gly Ala
             10                  15                  20 aac gag gcc gat gcc gac tgc ctg tcc gga aga tac aag ggt ccc tgt     211
Asn Glu Ala Asp Ala Asp Cys Leu Ser Gly Arg Tyr Lys Gly Pro Cys
         25                  30                  35 gcc gtc tgg gac aac gag acc tgt cgt cgt gtg tgc aag gag gag gga     259
Ala Val Trp Asp Asn Glu Thr Cys Arg Arg Val Cys Lys Glu Glu Gly
     40                  45                  50 cgc tcc agt ggc cac tgc agc ccc agt ctg aag tgc tgg tgc gaa gga     307
Arg Ser Ser Gly His Cys Ser Pro Ser Leu Lys Cys Trp Cys Glu Gly
 55                  60                  65 tgc taaatccatg agcaattagc atgaacgttc tgaaaagcgc gtttagctct          360
Cys
```

```
                                                                        70
ccactactta cgacatattc tatgctgcaa tattgaaaat ctaataaaca aaactaatgt        420
acattaaaaa aaaaaaaaaa aaaaaaaaaa aaaaaaaggg cggccgcgac ctgcaggcat       480
gcaagctt                                                                488

<210> SEQ ID NO 2
<211> LENGTH: 70
<212> TYPE: PRT
<213> ORGANISM: Drosophila melanogaster

<400> SEQUENCE: 2

Met Met Gln Ile Lys Tyr Leu Phe Ala Leu Phe Ala Val Leu Met Leu
 1               5                  10                  15

Val Val Leu Gly Ala Asn Glu Ala Asp Ala Asp Cys Leu Ser Gly Arg
            20                  25                  30

Tyr Lys Gly Pro Cys Ala Val Trp Asp Asn Glu Thr Cys Arg Arg Val
         35                  40                  45

Cys Lys Glu Glu Gly Arg Ser Ser Gly His Cys Ser Pro Ser Leu Lys
     50                  55                  60

Cys Trp Cys Glu Gly Cys
 65                  70

<210> SEQ ID NO 3
<211> LENGTH: 167
<212> TYPE: DNA
<213> ORGANISM: Drosophila melanogaster
<220> FEATURE:
<221> NAME/KEY: CDS
<222> LOCATION: (21)...(152)

<400> SEQUENCE: 3
gagagatccc ccgcggtggt gac tgc ctg tcc gga aga tac aag ggt ccc tgt       53
                      Asp Cys Leu Ser Gly Arg Tyr Lys Gly Pro Cys
                       1               5                  10 gcc gtc tgg gac aac gag acc tgt cgt cgt gtg tgc aag gag gag gga       101
Ala Val Trp Asp Asn Glu Thr Cys Arg Arg Val Cys Lys Glu Glu Gly
             15                  20                  25 cgc tcc agt ggc cac tgc agc ccc agt ctg aag tgc tgg tgc gaa gga       149
Arg Ser Ser Gly His Cys Ser Pro Ser Leu Lys Cys Trp Cys Glu Gly
         30                  35                  40 tgc taaggatccg cgcgc                                                   167
Cys

<210> SEQ ID NO 4
<211> LENGTH: 44
<212> TYPE: PRT
<213> ORGANISM: Drosophila melanogaster

<400> SEQUENCE: 4

Asp Cys Leu Ser Gly Arg Tyr Lys Gly Pro Cys Ala Val Trp Asp Asn
 1               5                  10                  15

Glu Thr Cys Arg Arg Val Cys Lys Glu Glu Gly Arg Ser Ser Gly His
            20                  25                  30

Cys Ser Pro Ser Leu Lys Cys Trp Cys Glu Gly Cys
         35                  40

<210> SEQ ID NO 5
<211> LENGTH: 236
<212> TYPE: DNA
<213> ORGANISM: Artificial Sequence
```

```
<220> FEATURE:
<223> OTHER INFORMATION: Synthetic sequence derived from plasmid
      pRPA-RD-186
<221> NAME/KEY: CDS
<222> LOCATION: (15)...(221)
<223> OTHER INFORMATION: Encodes the ubiquitin - drosomycin fusion peptide

<400> SEQUENCE: 5
gaattgaaga cgcc atg cag atc aag tac ttg ttc gcc ctc ttc gct gtc         50
             Met Gln Ile Lys Tyr Leu Phe Ala Leu Phe Ala Val
              1               5                  10 ctg atg ctg gtg gtg ctg gga gcc aac gag gcc gat gcc gac tgc ctg         98
Leu Met Leu Val Val Leu Gly Ala Asn Glu Ala Asp Ala Asp Cys Leu
         15                  20                  25 tcc gga aga tac aag ggt ccc tgt gcc gtc tgg gac aac gag acc tgt        146
Ser Gly Arg Tyr Lys Gly Pro Cys Ala Val Trp Asp Asn Glu Thr Cys
     30                  35                  40 cgt cgt gtg tgc aag gag gag gga cgc tcc agt ggc cac tgc agc ccc        194
Arg Arg Val Cys Lys Glu Glu Gly Arg Ser Ser Gly His Cys Ser Pro
 45                  50                  55                  60 agt ctg aag tgc tgg tgc gaa gga tgc taaggatccg cgcgc                   236
Ser Leu Lys Cys Trp Cys Glu Gly Cys
                 65

<210> SEQ ID NO 6
<211> LENGTH: 69
<212> TYPE: PRT
<213> ORGANISM: Artificial Sequence
<220> FEATURE:
<223> OTHER INFORMATION: The ubiquitin - drosomycin fusion peptide

<400> SEQUENCE: 6

Met Gln Ile Lys Tyr Leu Phe Ala Leu Phe Ala Val Leu Met Leu Val
 1               5                  10                  15

Val Leu Gly Ala Asn Glu Ala Asp Ala Asp Cys Leu Ser Gly Arg Tyr
             20                  25                  30

Lys Gly Pro Cys Ala Val Trp Asp Asn Glu Thr Cys Arg Arg Val Cys
         35                  40                  45

Lys Glu Glu Gly Arg Ser Ser Gly His Cys Ser Pro Ser Leu Lys Cys
     50                  55                  60

Trp Cys Glu Gly Cys
 65

<210> SEQ ID NO 7
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 7
aattcccgaa gacgacatgc agatcaagt                                         29

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
acttgatctg catgtcgtct tcggg                                             25
```

<210> SEQ ID NO 9
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 9
gagagatccc ccgcggtggt gactgcctgt ccggaagata caagggtccc tgtgccgtct    60
gggacaacga gacctgtcgt cgtgtgtgca aggaggaggg                          100

<210> SEQ ID NO 10
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 10
gcgcgcggat ccttagcatc cttcgcacca gcacttcaga ctggggctgc agtggccact    60
ggagcgtccc tcctccttgc acacacgacg                                     90

<210> SEQ ID NO 11
<211> LENGTH: 85
<212> TYPE: DNA
<213> ORGANISM: Artificial Sequence
<220> FEATURE:
<223> OTHER INFORMATION: Synthetic oligonucleotide

<400> SEQUENCE: 11
agggccccct agggtttaaa cggccagtca ggccgaattc gagctcggta cccggggatc    60
ctctagagtc gacctgcagg catgc                                          85

<210> SEQ ID NO 12
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 12
ccctgaacca ggctcgaggg cgcgccttaa ttaaaagctt gcatgcctgc aggtcgactc    60
tagagg                                                               66

<210> SEQ ID NO 13
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 13
cgggccagtc aggccacact taattaagtt taaacgcggc cccggcgcgc ctaggtgtgt    60
gctcgagggc ccaacctcag tacctggttc agg                                 93

<210> SEQ ID NO 14
<211> LENGTH: 93
<212> TYPE: DNA
<213> ORGANISM: Artificial Sequence
<220> FEATURE:
<223> OTHER INFORMATION: Synthetic oligonucleotide

<400> SEQUENCE: 14
ccggcctgaa ccaggtactg aggttgggcc ctcgagcaca cacctaggcg cgccggggcc        60
gcgtttaaac ttaattaagt gtggcctgac tgg                                    93

<210> SEQ ID NO 15
<211> LENGTH: 44
<212> TYPE: PRT
<213> ORGANISM: Artificial Sequence
<220> FEATURE:
<223> OTHER INFORMATION: Drosomycin core sequence
<221> NAME/KEY: VARIANT
<222> LOCATION: (1)...(1)
<223> OTHER INFORMATION: Perferably Asp
<221> NAME/KEY: VARIANT
<222> LOCATION: (3)...(3)
<223> OTHER INFORMATION: Preferably Leu
<221> NAME/KEY: VARIANT
<222> LOCATION: (10)...(10)
<223> OTHER INFORMATION: Preferably Pro
<221> NAME/KEY: VARIANT
<222> LOCATION: (12)...(12)
<223> OTHER INFORMATION: Preferably Ala
<221> NAME/KEY: VARIANT
<222> LOCATION: (18)...(18)
<223> OTHER INFORMATION: Preferably Thr
<221> NAME/KEY: VARIANT
<222> LOCATION: (20)...(20)
<223> OTHER INFORMATION: Preferably Arg
<221> NAME/KEY: VARIANT
<222> LOCATION: (22)...(22)
<223> OTHER INFORMATION: Preferably Val
<221> NAME/KEY: VARIANT
<222> LOCATION: (24)...(24)
<223> OTHER INFORMATION: Preferably Lys
<221> NAME/KEY: VARIANT
<222> LOCATION: (32)...(32)
<223> OTHER INFORMATION: Preferably His
<221> NAME/KEY: VARIANT
<222> LOCATION: (34)...(34)
<223> OTHER INFORMATION: Preferably Ser
<221> NAME/KEY: VARIANT
<222> LOCATION: (38)...(38)
<223> OTHER INFORMATION: Preferably Lys
<221> NAME/KEY: VARIANT
<222> LOCATION: (40)...(40)
<223> OTHER INFORMATION: Preferably Trp
<221> NAME/KEY: VARIANT
<222> LOCATION: (42)...(42)
<223> OTHER INFORMATION: Preferably Glu
<221> NAME/KEY: VARIANT
<222> LOCATION: (43)...(43)
<223> OTHER INFORMATION: Preferably Gly
<221> NAME/KEY: VARIANT
<222> LOCATION: (4)...(9)
<223> OTHER INFORMATION: Preferably Ser Gly Arg Tyr Lys Gly
<221> NAME/KEY: VARIANT
<222> LOCATION: (13)...(17)
<223> OTHER INFORMATION: Preferably Val Trp Asp Asn Glu
<221> NAME/KEY: VARIANT
<222> LOCATION: (21)...(21)
<223> OTHER INFORMATION: Preferably Arg
<221> NAME/KEY: VARIANT
<222> LOCATION: (25)...(31)
<223> OTHER INFORMATION: Preferably Glu Glu Gly Arg Ser Ser Gly
<221> NAME/KEY: VARIANT
<222> LOCATION: (35)...(37)
<223> OTHER INFORMATION: Preferably Pro Ser Leu

<400> SEQUENCE: 15

-continued

```
Xaa Cys Xaa Xaa Xaa Xaa Xaa Xaa Xaa Xaa Cys Xaa Xaa Xaa Xaa Xaa
 1           5                   10                  15

Xaa Xaa Cys Xaa Xaa Xaa Cys Xaa Xaa Xaa Xaa Xaa Xaa Xaa Xaa Xaa
         20              25                  30

Cys Xaa Xaa Xaa Xaa Xaa Cys Xaa Cys Xaa Xaa Cys
         35              40
```

CHIMERIC GENE ENCODING DROSOMYCIN, VECTOR CONTAINING IT AND PRODUCTION OF DISEASE-RESISTANT TRANSGENIC PLANTS

CROSS-REFERENCE TO RELATED APPLICATIONS

This application is a continuation of and claims priority from PCT/FR98/01462, which was filed on Jul. 8, 1998 and which published in French on Jan. 21, 1999, which in turn claims priority from French Application Nos. 97/09,115 filed on Jul. 11, 1997 and 97/09,663 filed on Jul. 24, 1997.

FIELD OF THE INVENTION

The subject of the present invention is a DNA sequence encoding drosomycin, a chimeric gene containing it, a vector containing the chimeric gene and a method of transforming plants and the disease-resistant transformed plants.

BACKGROUND OF THE INVENTION

There is nowadays an increasing need to make plants resistant to diseases, in particular fungal diseases, in order to reduce or even avoid the need to resort to treatments with antifungal protection products, so as to protect the environment. One way of increasing this resistance to diseases consists in transforming plants so that they produce substances capable of providing their defence against these diseases.

Various substances of natural origin, in particular peptides, are known which have bactericidal or fungicidal properties, in particular against fungi responsible for plant diseases. However, the problem consists in finding such substances which not only can be produced by transformed plants, but can still preserve their bactericidal or fungicidal properties and confer them on the said plants. For the purposes of the present invention, bactericide or fungicide is understood to mean both the actual bactericidal or fungicidal properties and the bacteriostatic or fungistatic properties.

Drosomycins are peptides produced by the larvae and adults of drosophila by induction following septic injury or the injection of a low dose of bacteria. A peptide has already been described as having certain antifungal and antibacterial properties in vitro, in particular in French patent application 2,725,992, where the peptide is obtained by induction in drosophila and purification. The gene encoding this same peptide has also been described by Fehlbaum et al. (1994). The possibility of integrating this gene into a plant to confer on it resistance to diseases of fungal or bacterial origin has, however, so far not been described.

It has now been found that the genes for drosomycins could be inserted into plants to confer on them properties of resistance to fungal diseases and to diseases of bacterial origin, providing a particularly advantageous solution to the problem set out above.

SUMMARY OF THE INVENTION

The invention concerns a chimeric gene containing a DNA sequence coding for drosomycin, a vector containing the chimeric gene, a method for transforming plants and the resulting transformed plants. The drosomycin produced by the plants provides them with resistance to diseases, in particular of fungal origin.

DETAILED DESCRIPTION OF THE INVENTION

Figure 1:
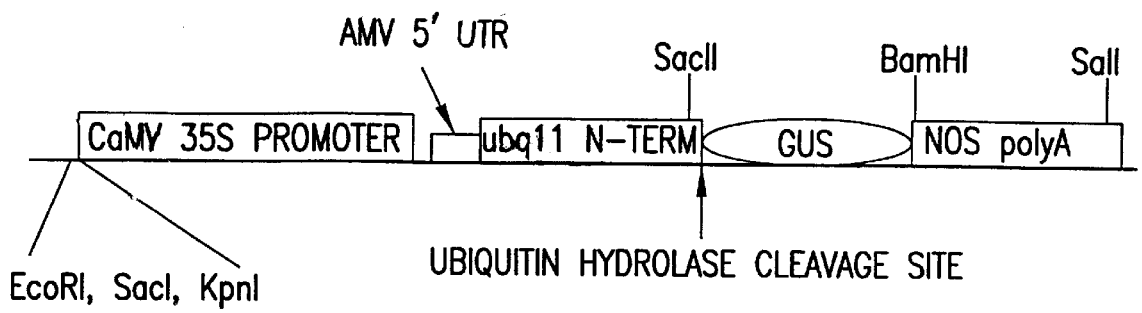
FIG. 1 shows a schematic diagram of a plasmid (pUGUS (118)) containing the CaMV 35S promoter driving expression of the alfalfa mosaic virus (AMV) 5' UTR, the N-terminal region of Arabidopsis thaliana ubiquitin gene (ubq11) and E. coli β-glucuronidase (GUS) gene.

The subject of the invention is therefore firstly a chimeric gene comprising a nucleic acid fragment encoding a drosomycin as well as heterologous regulatory elements at positions 5' and 3' capable of functioning in plants and a vector for the transformation of plants containing this chimeric gene. It also comprises a transformed plant cell containing at least one nucleic acid fragment encoding drosomycin and a disease-resistant plant containing the said cell. It finally relates to a method of transforming plants to make them resistant to diseases, in which a gene encoding drosomycin is inserted.

Drosomycin is understood to mean according to the invention any peptide capable of being isolated from the larvae and adults of drosophila by induction following a septic injury or the injection of a low dose of bacteria, these peptides comprising at least 44 amino acids and 8 cystein residues forming disulphide bridges with each other.

Advantageously, drosomycin essentially comprises the peptide sequence of formula (I) (SEQ ID NO: 15) below:

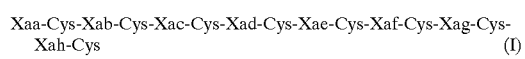

$$\text{Xaa-Cys-Xab-Cys-Xac-Cys-Xad-Cys-Xae-Cys-Xaf-Cys-Xag-Cys-Xah-Cys} \quad (I)$$

in which

Xaa represents a peptide residue comprising at least 1 amino acid,

Xab represents a peptide residue of 8 amino acids,

Xac represents a peptide residue of 7 amino acids,

Xad represents a peptide residue of 3 amino acids,

Xae represents a peptide residue of 9 amino acids,

Xaf represents a peptide residue of 5 amino acids,

Xag represents a peptide residue of one amino acid, and

Xah represents a peptide residue of 2 amino acids.

Advantageously, Xab and/or Xad and/or Xac comprise at least one basic amino acid. More advantageously, Xab comprises at least 2 basic amino acids, preferably 2 and/or Xad and/or Xaf comprise at least 1 basic amino acid, preferably 1. Basic amino acid is understood to mean according to the invention the amino acids chosen from lysine, arginine or homoarginine.

Preferably,

Xaa represents the peptide sequence Xaa'-Asp- in which Xaa' represents $NH_2$ or a peptide residue comprising at least 1 amino acid, and/or Xab represents the peptide sequence -Leu-Xab'-Pro- in which Xab' represents a peptide residue of 6 amino acids, and/or Xac represents the peptide sequence -Ala-Xac'-Thr- in which Xac' represents a peptide residue of 5 amino acids, and/or Xad represents the peptide sequence -Arg-Xad'-Val, in which Xad' represents a peptide residue of one amino acid, and/or Xae represents the peptide sequence -Lys-Xae'-His- in which Xae' represents a peptide residue of 7 amino acids, and/or Xaf represents the peptide sequence -Ser-Xaf'-Lys- in which Xaf' represents a peptide residue of 3 amino acids, and/or Xag represents Trp, and/or Xah represents the peptide residue Glu-Gly.

Preferably,

Xab' represents the peptide sequence Ser-Gly-Arg-Tyr-Lys-Gly, and/or

Xac' represents the peptide sequence Val-Trp-Asp-Asn-Glu, and/or

Xad' represents Arg, and/or

Xae' represents the peptide sequence Glu-Glu-Gly-Arg-Ser-Ser-Gly, and/or

Xaf' represents the peptide sequence Pro-Ser-Leu.

According to a more preferred embodiment of the invention, drosomycin is the peptide sequence represented by SEQ ID NO: 4 and the homologous peptide sequences.

Homologous peptide sequences is understood to mean any equivalent sequence comprising at least 65% homology with the sequence represented by SEQ ID NO: 4, it being understood that the 8 cystein residues and the number of amino acids separating them remain identical, some amino acids being replaced with different but equivalent amino acids at sites which do not induce substantial modification of the antifungal or antibacterial activity of the said homologous sequence. Preferably, the homologous sequences comprise at least 75% homology, more preferably at least 85% homology, still more preferably 90% homology.

The terminal $NH_2$ residue may exhibit a post-translational modification, for example an acetylation, in the same way that the C-terminal residue may exhibit a post-translational modification, for example an amidation.

Peptide sequence mainly comprising the peptide sequence of general formula (I) is understood to mean not only the sequences defined above, but also such sequences comprising at either of their ends, or both, peptide residues, in particular which are necessary for their expression and targeting in plant cells or in plants.

It is in particular "full-length" drosomycin represented by SEQ ID NO: 2.

It is in particular a "peptide-drosomycin" or "drosomycin-peptide", advantageously "peptide-drosomycin" fusion peptide, the cutting of which by the enzymatic systems of plant cells allows the liberation of the drosomycin defined above. The peptide fused with drosomycin may be a signal peptide or a transit peptide which makes it possible to control and orient the production of drosomycin in a specific manner in a part of the plant cell or of the plant, such as for example the cytoplasm, the cell membrane, or in the case of plants in a specific type of cell compartment or of tissues or in the extracellular matrix.

According to one embodiment, the transit peptide may be a chloroplast or mitochondrial addressing signal, which is then cleaved in the chloroplasts or mitochondria.

According to another embodiment of the invention, the signal peptide may be an N-terminal or "prepeptide" signal, optionally in combination with a signal responsible for retaining the protein in the endoplasmic reticulum, or a vacuolar addressing peptide or "propeptide". The endoplasmic reticulum is the site where the "cellular machinery" carries out the operations of maturation of the protein produced, such as for example the cleavage of the signal peptide.

The transit peptides may be either single, or double, and in this case optionally separated by an intermediate sequence, that is to say comprising, in the direction of transcription, a sequence encoding a transit peptide for a plant gene encoding a plastid localization enzyme, a portion of sequence of the N-terminal mature portion of a plant gene encoding a plastid localization enzyme, and then a sequence encoding a second transit peptide for a plant gene encoding a plastid localization enzyme, as described in Patent EP 0 508 909.

As transit peptide useful according to the invention, there may be mentioned in particular the signal peptide of the tobacco PR-1α gene (WO 95/19443), or alternatively the ubiquitin represented, fused with d drosomycin by SEQ ID NO: 6.

The fusion peptide "ubiquitin-arosomycln" and its coding sequence are also included in the present invention, in particular described by SEQ ID NO: 5.

The present invention therefore relates to a chimeric gene comprising a sequence encoding drosomycin as well as heterologous regulatory elements at positions 5' and 3' capable of functioning in plants, the coding sequence comprising at least one DNA sequence encoding drosomycin as defined above.

The DNA sequence may be obtained according to standard methods of isolation and purification from drosophila, or alternatively by synthesis according to the usual techniques of successive hybridizations of synthetic oligonucleotides. These techniques are in particular described by Ausubel et al.

According to one embodiment of the invention, the DNA sequence encoding drosomycin comprises the DNA sequence described by bases 21 to 152 of SEQ ID NO: 3, a sequence homologous or complementary to the said sequence.

According to another embodiment of the invention, the DNA sequence encoding "full-length" drosomycin comprises the DNA sequence described by bases 101 to 310 of SEQ ID NO: 1, a sequence homologous or complementary to the said sequence.

According to another embodiment of the invention, the DNA sequence encoding the "peptide-heliomycin" fusion peptide comprises the DNA sequence described by bases 15 to 221 of SEQ ID NO: 5, a homologous sequence or a sequence complementary to the said sequences.

"Homologous" is understood to mean according to the invention any DNA sequence having one or more sequence modifications compared with the nucleotide sequence described by SEQ ID NOS: 1, 3 and 5 and encoding drosomycin, "full-length" drosomycin or the "peptide-drosomycin" fusion peptide. These modifications may be obtained according to the usual mutation techniques, or alternatively by choosing the synthetic oligonucleotides used in the preparation of the said sequence by hybridization. In the light of the multiple combinations of nucleic acids which can lead to the expression of the same amino acid, the differences between the reference sequence described by the sequence identifiers No. 1, 3 or 5 and the corresponding homologue may be substantial, all the more so since they are small-sized DNA fragments which can be made by chemical synthesis. Advantageously, the degree of homology will be at least 70% relative to the reference sequence, preferably at least 80%, more preferably at least 90%. These modifications are generally neutral, that is to say that they do not affect the primary sequence of the resulting drosomycin or fusion peptide.

"Plan t cell" is understood to mean according to the invention any cell derived from a plant and capable of constituting undifferentiated tissues such as calli, differentiated tissues such as embryos, plant portions, plants or seeds.

"Plant" is understood to mean according to the invention any differentiated multicellular organism capable of photosynthesis, in particular monocotyledonous or dicotyledonous plants, more particularly crop plants intended or not as animal feed or for human consumption, such as maize, wheat, colza, soya bean, rice, sugar cane, beet, tobacco, cotton and the like.

The regulatory elements necessary for the expression of the DNA sequence encoding drosomycin are well known to persons skilled in the art according to the plant. They comprise in particular promoter sequences, transcription activators, terminator sequences, including start and stop codons. The means and methods for identifying and selecting the regulatory elements are well known to persons skilled in the art. As promoter regulatory sequence in plants, there may be used any promoter sequence of a gene which is naturally expressed in plants, in particular a promoter of bacterial, viral or plant origin such as, for example, that of a ribulose-biscarboxylase/oxygenase (RuBisCO) small sub-unit gene or of a plant virus gene such as, for example, that of the cauliflower mosaic (CAMV 19S or 35S), or a promoter inducible by pathogens such as tobacco PR-la, it being possible to use any known suitable promoter. Preferably, a regulatory promoter sequence is used which promotes the overexpression of the coding sequence constitutively or inducibly upon attack by a pathogen, such as for example that comprising at least one histone promoter as described in application EP 0 507 698.

According to the invention, it is also possible to use, in combination with the regulatory promoter sequence, other regulatory sequences, which are situated between the promoter and the coding sequence, such as transcription enhancers, such as for example the translational enhancer of the tobacco mosaic virus (TMV) described in application WO 87/07644, or of the tobacco etch virus (TEV) described by Carrington & Freed.

As regulatory terminator or polyadenylation sequence, there may be used any corresponding sequence of bacterial origin, such as for example the *Agrobacterium tumefaciens* nos terminator, or alternatively of plant origin, such as for example a histone terminator as described in application EP 0,633,317.

The present invention also relates to an integrating vector for the transformation of plants containing at least one chimeric gene as defined above.

The subject of the invention is also a method of transforming plant cells by integration of at least one chimeric gene as defined above, which transformation may be obtained by any known appropriate means, widely described in the specialist literature and in particular the applications cited in the present application.

One series of methods consists in bombarding cells or protoplasts with particles to which the DNA sequences are attached.

Another series of methods consists in using, as means of transferring into the plant, a chimeric gene inserted into an *Agrobacterium tumefaciens* Ti plasmid or an *Agrobacterium rhizogenes* Ri plasmid.

Other methods may be used, such as microinjection or electroporation.

Persons skilled in the art will choose the appropriate method according to the nature of the plant, in particular its monocotyledonous or dicotyledonous character.

For the methods of transforming plant cells and of regenerating plants, there may be mentioned the following patents and patent applications: U.S. Pat. Nos. 4,459,355, 4,536,475, 5,464,763, 5,177,010, 5,187,073, EP 267,159, EP 604 662, EP 672 752, U.S. Pat. Nos. 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253, 5,405,765, EP 442 174, EP 486 233, EP 486 234, EP 539 563, EP 674 725, WO 91/02071 and WO 95/06128.

The subject of the present invention is also the plant cells, of monocotyledonous or dicotyledonous plants, in particular of crops, which are transformed and which contain in their genome an effective quantity of a gene comprising a sequence encoding the drosomycin defined above.

The subject of the present invention is also the plants containing transformed cells, in particular the plants regenerated from the transformed cells. The regeneration is obtained by any appropriate method which depends on the nature of the species, as for example described in the above patents and applications.

The subject of the present invention is also the transformed plants derived from the cultivation and/or the crossing of the above regenerated plants, as well as the seeds of the transformed plants.

The plants thus transformed are resistant to certain diseases, in particular to certain fungal diseases. Because of this, the DNA sequence encoding drosomycin may be integrated with the main objective of producing plants resistant to the said diseases, the drosomycin being effective against fungal diseases such as those caused by Botrytis, in particular *Botrytis cinerea* (mycelium or spores), Cercospora, in particular *Cercospora beticola*, Septoria, in particular *Septoria tritici*, or Fusarium, in particular *Fusarium culmorum* (mycelium or spores) or *Fusarium graminearum*.

The chimeric gene may also advantageously comprise at least one selectable marker, such as one or more genes for tolerance to herbicides.

The DNA sequence encoding drosomycin may also be integrated as a selectable. marker during the transformation of plants with other sequences encoding other peptides or proteins of interest, such as for example genes for tolerance to herbicides.

Such genes for tolerance to herbicides are well known to persons skilled in the art and are in particular described in Patent Applications EP 115 673, WO 87/04181, EP 337 899, WO 96/38567 or WO 97/04103.

Of course, the cells and plants transformed according to the invention may comprise, in addition to the sequence encoding drosomycin, other heterologous sequences encoding proteins of interest, such as other additional peptides capable of conferring on the plant resistance to other diseases of bacterial or fungal origin, and/or other sequences encoding proteins for tolerance to herbicides and/or other sequences encoding proteins for resistance to insects, such as the Bt proteins in particular.

The other sequences may be integrated by means of the same vector comprising a chimeric gene, which comprises a first sequence encoding drosomycin and at least one other sequence encoding another peptide or protein of interest.

They may also be integrated by means of another vector comprising at least the said other sequence, according to the usual techniques defined above.

The plants according to the invention may also be obtained by the crossing of parents, one carrying the gene according to the invention encoding drosomycini, the other carrying a gene encodina at least one other peptide or protein of interest.

The present invention zinally relates to a method of cultivating the transformed plants according to the invention, the method consisting in planting the seeds of the said transformed plants in an area of a field appropriate for the cultivation of the said plants, in applying to the said area of the said field an agrochemical composition, without substantially affecting the said seeds or the said transformed plants, and then in harvesting the cultivated plants when they reach the desired maturity and optionally in separating the seeds from the harvested plants.

Agrochemical composition is understood to mean according to the invention any agrochemical composition comprising at least one active product having one of the following activities: herbicidal, fungicidal, bactericidal virucidal or insecticidal activity.

According to a preferred embodiment of the method of cultivation according to the invention, the agrochemical composition comprises at least one active product having at least one fungicidal and/or bactericidal activity, more preferably exhibiting an activity complementary to that of the drosomycin produced by the transformed plants according to the invention.

Product exhibiting an activity complementary to that of drosomycin is understood to mean according to the invention a product exhibiting a complementary activity spectrum, that is to say a product which will be active against attacks by contaminants (fungi, bacteria or viruses) which are insensitive to drosomycin, or alternatively a product whose activity spectrum covers that of drosomycin, completely or in part, and whose dose for application will be substantially reduced because of the presence of the drosomycin produced by the transformed plant.

The examples below make it possible to illustrate the invention, the preparation of the chimeric gene, of the integrating vector, of the transformed plants and their resistance to various diseases of fungal origin. FIGS. 1 to 7 in the annex describe the schematic structures of some plasmids prepared for the construction of the chimeric genes. In these figures, the different restriction sites are marked in italics.

EXAMPLE 1

Construction of the Chimeric Genes

All the techniques used below are standard laboratory techniques. The detailed protocols for these techniques are in particular described in Ausubel et al.

pRPA-RD-180:

A whole cDNA clone encoding drosomycin described by Fehlbaum et al. (SEQ ID NO. 1) is inserted into the plasmid pCR-1000 (INVITROGEN) as EcoRI-HindIII fragment.

pRPA-RD-182:

Creation of a region encoding so-called "full-length" drosomycin (corresponding to the pre-pro peptide) by removing the nontranscribed region in 5' and by eliminating the first ATG codon.

The plasmid pRPA-RD-180 is digested with the restriction enzymes ScaI and EcoRI, and the large DNA fragment is purified. A double-stranded synthetic oligonucleotide comprising SEQ ID NOS. 7 and 8 (Oligo 1) is then linked to the purified DNA sequence derived from pRPA-RD-180:

Oligo 1:

```
SEQ ID NO. 7  5'  AATTCCCGAAGACGACATGCAGATCAAGT 3'

SEQ ID NO. 8  3'       GGGCTTCTGCTGTACGTCTAGTTCA 5'
``` pRPA-RD-183:

Creation of a sequence encoding mature drosomycin which does not comprise the nontranscribed region in 3'.

The two complementary synthetic oligonucleotides, SEQ ID NO. 9 (Oligo 2) and SEQ ID NO. 10 (Oligo 3), are hybridized at 65° C. for 5 minutes and then by a slow reduction of the temperature to 30° C. over 30'.

```
SEQ ID NO. 9 (Oligo 2):
5' GAGAGATCCC CCGCGGTGGT GACTGCCTGT CCGGAAGATA
   CAAGGGTCCC TGTGCCGTCT GGGACAACGA GACCTGTCGT
   CGTGTGTGCA AGGAGGAGGG 3'

SEQ ID NO:10 (Oligo 3):
5' GCGCGCGGAT CCTTAGCATC CTTCGCACCA GCACTTCAGA
   CTGGGGCTGC AGTGGCCACT GGAGCGTCCC TCCTCCTTGC
   ACACACGACG 3'
```

After hybridization between Oligo 2 and Oligo 3, the DNA remaining single-stranded serves as template for the Klenow fragment of E. coli polymerase I (under the standard conditions recommended by the manufacturer (New England Biolabs)) for the creation of the double-stranded oligonucleotide. This double-stranded oligonucleotide is then digested with the restriction enzymes SacII and EcoRI and cloned into the plasmid pBS II SK(−) (Stratagene) digested with the same restriction enzymes. A clone is then obtained comprising the region encoding mature drosomycin situated between the SacII and BamHI restriction sites (SEQ ID NO: 3).

pRPA-RD-186:

Removal of the nontranscribed 3' region from the region encoding full-length drosomycin of pRPA-RD-182.

The plasmid pRPA-RD-182 is digested with the restriction enzymes BspEI and KpnI, and the large DNA fragment is purified. The plasmid pRPA-RD-183 is then digested with the restriction enzymes BspEI and KpnI, and the small DNA fragment is purified. These two purified fragments are then linked so as to obtain a plasmid containing the region encoding the pre-pro peptide of drosomycin whose first ATG codon and the two noncoding regions in 5' and 3' have been eliminated (SEQ ID NO: 5).

pRPA-RD-187:

Creation of a vector for expression in plants comprising the sequence encoding the mature form of drosomycin.

The plasmid pUGUS(118), derived from pUC-19, was obtained from Dr. Richard Vierstra of the University of Wisconsin (plasmid not described). This plasmid, whose schematic structure is represented in FIG. 1, contains the CaMV 35S promoter which directs the expression of an RNA containing the untranslated sequence in 5' of the alfalfa mosaic virus (AMV 5' UTR; Brederode et al., 1980), the N-terminal region of the *Arabidopsis thaliana* ubiquitin gene ubq11 up to the ubiquitin hydrolase cleavage site (N-term ubq11; Callis et al., 1993) which is fused in the same reading frame with the *E. coli* β-glucuronidase gene (GUS; Jefferson et al., 1987), followed by the polyadenylation site of the *Agrobacterium tumefaciens* nopaline synthase gene (NOS polyA; Bevan et al., 1983).

Figure 2:
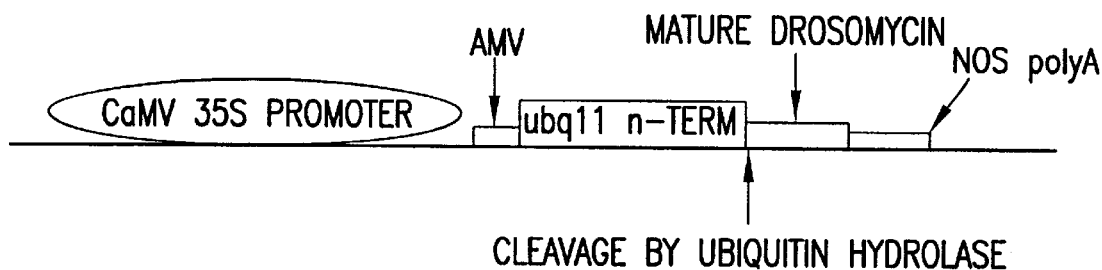
FIG. 2 shows a schematic diagram of a plasmid containing the duplicated CaMV 35S promoter driving expression of the alfalfa mosaic virus (AMV) 5' UTR, the N-terminal region of Arabidopsis thaliana ubiquitin gene (ubq11) and the mature form of drosomycin.

The plasmid pUGUS(118) is digested with the restriction enzymes SacII and BamHI and the large DNA fragment is purified. The plasmid pRPA-RD-183 is digested with the restriction enzymes SacII and BainHI and the small DNA fragment containing the region encoding the mature form of drosomycin is then purified. The two purified DNA fragments are linked together in a cassette for expression in plants which synthesize a ubiquitin-drosomycin fusion protein in the cytoplasm of plant cells. The schematic structure of this expression cassette is represented in FIG. 2. Under the action of ubiquitin hydrolase on this fusion protein, the mature drosomycin is liberated into the cytoplasm of the plant cells.

pRPA-RD-188:

Creation of a plant expression vector comprising the full length of the sequence encoding drosomycin (pre-pro).

Figure 3:
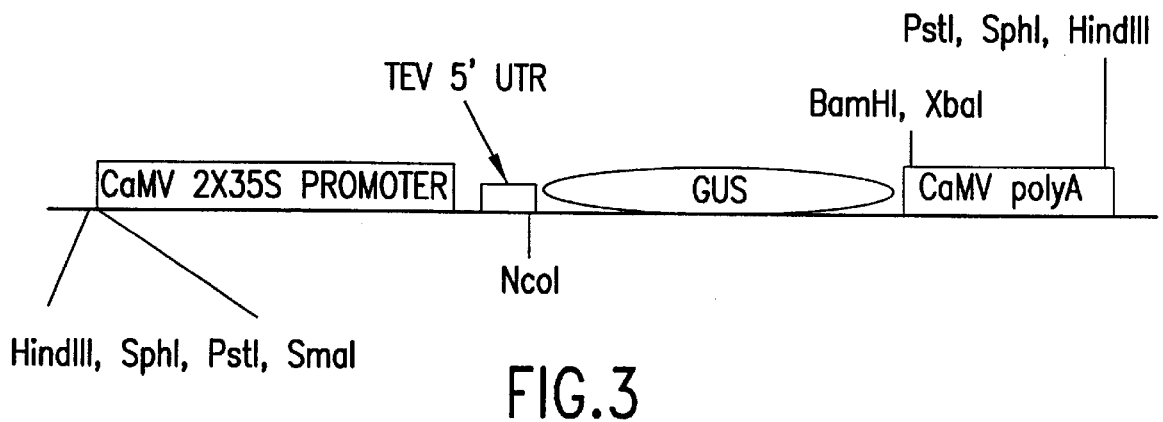
FIG. 3 shows a schematic diagram of a plasmid (pRTL-2 GUS) containing the duplicated CaMV 35S promoter driving expression of the tobacco etch virus (TEV) 5' UTR and the E. coli β-glucuronidase (GUS) gene.

The plasmid pRTL-2 GUS, derived from the plasmid pUC-19, was obtained from Dr. Jim Carrington (Texas A&M University, not described). This plasmid, whose schematic structure is represented in FIG. 3, contains the duplicated CaMV 35S promoter isolated from the cauliflower mosaic virus (CaMV 2×35S promoter; Odell et al., 1985) which directs the expression of an RNA containing tobacco etch virus 5' untranslated sequence (TEV 5' UTR; Carrington & Freed, 1990), the *E. coli* β-glucuronidase gene (GUS, Jefferson et al., 1987) followed by the CaMV 35S RNA polyadenylation site (CaMV polyA; Odell et al., 1985).

Figure 4:
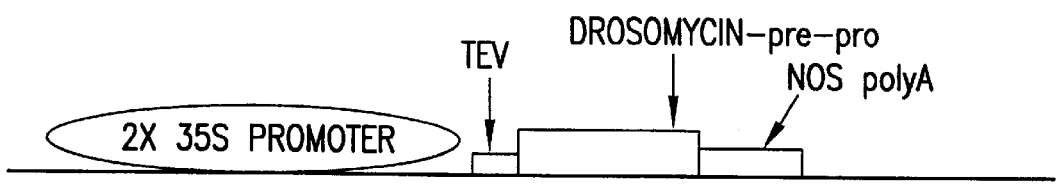
FIG. 4 shows a schematic diagram of a plasmid containing the duplicated CaMV 35S promoter driving expression of the tobacco etch virus (TEV) 5' UTR and the drosomycin gene encoding the pre-pro drosomycin protein.

The plasmid pRTL-2 GUS is digested with the restriction enzymes NcoI and BamHI and the large DNA fragment is purified. The plasmid pRPA-RD-186 is digested with the restriction enzymes BbsII and BamHI and the small DNA fragment containing the region encoding drosomycin pre-pro is purified. The two purified DNA fragments are then linked together in a cassette for expression in plants which synthesize a drosomycin pre-pro protein. The schematic structure of this expression cassette is represented in FIG. 4. "Pre-pro-drosomycin" represents the drosomycin coding region of pRPA-RD-186. The drosomycin is transported to the extracellular matrix of the plant by the action of a signal peptide (pre-pro).

pRPA-RD-195:

Creation of a plasmid containing a modified multiple cloning site.

The plasmid pRPA-RD-195 is a plasmid derived from pUC-19 which contains a modified multiple cloning site. The complementary synthetic oligonucleotides SEQ ID NO. 11 (Oligo 4)and SEQ ID NO. 12 (Oligo 5) below are hybridized and made double-stranded according to the procedure described for pRPA-RD-183.

```
SEQ ID NO. 11 (Oligo 4):
5' AGGGCCCCCT AGGGTTTAAA CGGCCAGTCA GGCCGAATTC
   GAGCTCGGTA CCCGGGGATC CTCTAGAGTC GACCTGCAGG
   CATGC 3'
```

```
SEQ ID NO. 12 (Oligo 5):
5' CCCTGAACCA GGCTCGAGGG CGCGCCTTAA TTAAAAGCTT
   GCATGCCTGC AGGTCGACTC TAGAGG       3'
```

Figure 5:
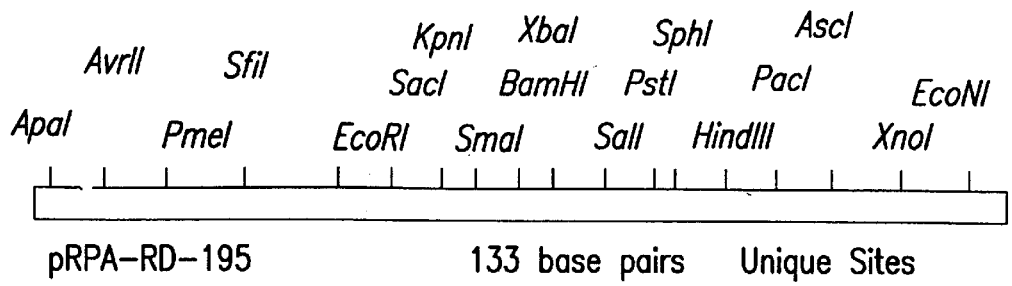
FIG. 5 shows a schematic diagram of the restriction enzyme sites found in the multiple cloning site of plasmid pRPA-RD-195.

The double-stranded oligonucleotide obtained is then linked in pUC-19 which has been previously digested with the restriction enzymes EcoRI and HindIII and made blunt-ended using the Klenow fragment of *E. coli* DNA polymerase I. A vector is obtained which contains multiple cloning sites to facilitate the introduction of the expression cassettes into an *Agrobacterium tumefaciens* vector plasmid. The schematic structure of this multiple cloning site is represented in FIG. 5.

pRPA-RD-190:

Introduction of the drosomycin expression cassette from pRPA-RD-187 into pRPA-RD-195.

The plasmid pRPA-RD-187 is digested with the restriction enzymes KpnI and SalI, and the DNA fragment containing the drosomycin expression cassette is purified. The purified fragment is then linked in pRPA-RD-195 which has been previously digested with the same restriction enzymes.

pRPA-RD-191:

Introduction of the drosomycin expression cassette from pRPA-RD-188 into pRPA-RD-195.

The plasmid pRPA-RD-188 is digested with the restriction enzyme HindIII and dephosphorylated with calf intestinal phosphatase. The DNA fragment containing the drosomycin expression cassette is purified. The purified fragment is then linked in pRPA-RP-195 which has been previously digested with the restriction enzyme HindIII.

pRPA-RD-174:

Plasmid derived from pRPA-BL-150A (EP 0,508,909) containing the bromoxynil tolerance gene of pRPA-BL-237 (EP 0,508,909).

The bromoxynil tolerance gene is isolated from pRPA-BL-237 by PCR gene amplification. The fragment obtained is blunt-ended and is cloned into the EcoRI site of pRPA-BL-150A which has been made blunt-ended by the action of Klenow polymerase under standard conditions. An *Agrobacterium tumefaciens* vector is obtained which contains the bromoxynil tolerance gene near its right border, a kanamycin tolerance gene near its left border and the multiple cloning site of pUC-19 between these two genes.

Figure 6:
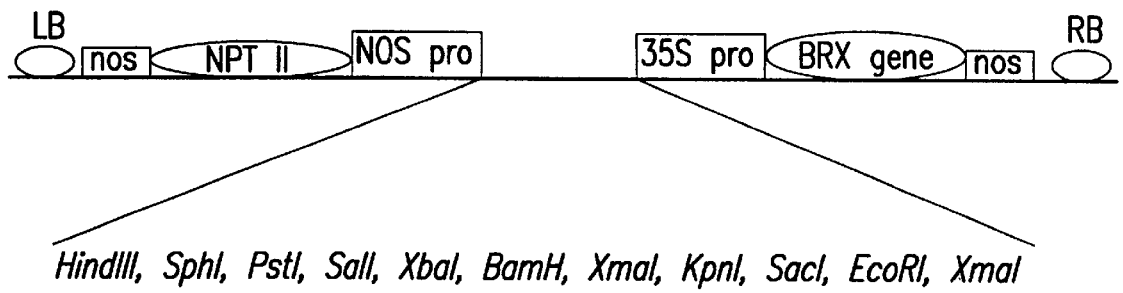
FIG. 6 shows a schematic diagram of a plasmid (pRPA-RD-174) containing the bromoxynil and kanamycin tolerance genes, a multiple cloning site, the Agrobacterium tumefaciens nopaline synthase polyadenylation site, the Agrobacterium tumefaciens nopaline synthase promoter, the E. coli neomycin phosphotransferase gene of the Tn5 transposon, the CaMV 35S promoter and the K. ozaenae nitrilase gene.

The schematic structure of pRPA-RD-174 is represented in FIG. 6. In this figure, "nos" represents the *Agrobacterium tumefaciens* nopaline synthase polyadenylation site (Bevan et al., 1983), "NOS pro" represents the *Agrobacterium tumefaciens* nopaline synthase promoter (Bevan et al., 1983), "NPT II" represents the neomycin phosphotransferase gene of the *E. coli* Tn5 transposon (Rothstein et al., 1981), "35S pro" represents the 35S promoter isolated from the cauliflower mosaic virus (Odell et al., 1985), "BRX" represents the nitrilase gene isolated from *K. ozaenae* (Stalker et al., 1988), "RB" and "LB" represent respectively the right and left borders of the sequence of an *Agrobacterium tumefaclens* Ti plasmid.

pRPA-RD-184:

Addition of a new unique restriction site to pRPA-RD-174.

The complementary synthetic oligonucleotides SEQ ID NO. 13 (Oligo 6)and SEQ ID NO. 14 (Oligo 7) below are hybridized and made double-stranded according to the procedure described for pRPA-RD-183.

SEQ ID NO. 13 (Oligo 6):
5' CGGGCCAGTC AGGCCACACT TAATTAAGTT TAAACGCGGC
    CCCGGCGCGC CTAGGTGTGT GCTCGAGGGC CCAACCTCAG
    TACCTGGTTC AGG  3'

SEQ ID NO. 14 (Oligo 7):
5' CCGGCCTGAA CCAGGTACTG AGGTTGGGCC CTCGAGCACA
    CACCTAGGCG CGCCGGGCC GCGTTTAAAC TTAATTAAGT
    GTGGCCTGAC TGG  3'

The hybridized double-stranded oligonucleotide (95 base pairs) is purified after separation on an agarose gel (3% Nusieve, FMC). The plasmid pRPA-RD-174 is digested with the restriction enzyme XmaI, and the large DNA fragment is purified. The two DNA fragments obtained are then linked.

A plasmid derived from pRPA-RD-174 is obtained which comprises other restriction sites between the bromoxynil tolerance gene and the kanamycin selectable marker gene.

Figure 7:
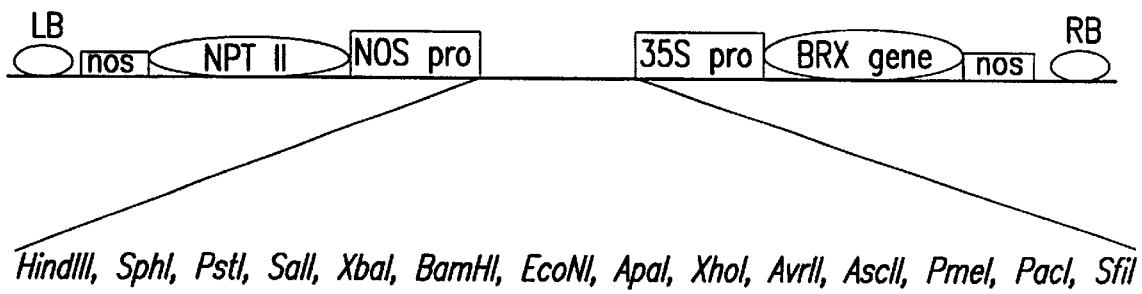
FIG. 7 shows a schematic diagram of a plasmid (pRPA-RD-184) derived from pRPA-RD-174 which comprises additional restriction sites.

The schematic structure of the plasmid pRPA-RD-184 is represented in FIG. 7, where the terms "nos", "NPT II", "NOS pro", "35S pro", "BRX gene", "RB" and "LB" have the same meaning as in FIG. 6.

pRPA-RD-192:

Creation of an Agrobacterium tumefaciens vector containing the gene construct encoding drosomycin directed towards the cytosol of the cells.

The plasmid pRPA-RD-190 is digested with the restriction enzymes ApaI and AscI, and the DNA fragment containing the drosomycin expression cassette is purified. The purified DNA fragment containing the drosomycin expression cassette is linked into pRPA-RD-184, after prior digestion with the same two enzymes. An *Agrobacterium tumefaciens* vector is thus obtained which contains the sequence encoding the drosomycin-ubiquitin fusion protein which leads to the expression of drosomycin in the cytosol of the plant cells.

pRPA-RD-193:

Creation of an *Agrobacterium tumefaciens* vector containing the gene construct encoding drosomycin directed towards the extracellular matrix.

The procedure described above is repeated with the plasmid pRPA-RD-191 and the restriction enzymes PmeI and AscI, replacing the plasmid pRPA-RD-190 and the restriction enzymes ApaI and AscI. An *Agrobacterium tumefaciens* vector is thus obtained which contains the sequence encoding the drosomycin pre-pro protein which leads to the expression of drosomycin in the extracellular matrix of the plant.

EXAMPLE 2

Herbicide Tolerance of Transformed Tobaccos.

2.1—Transformation

The vectors pRPA-RD-192 and pRPA-RD-193 are introduced into the *Agrobacterium tumefaciens* EHA101 strain (Hood et al., 1987) carrying the cosmid pTVK291 (Komari et al., 1986). The transformation technique is based on the procedure of Horsh et al. (1985).

2.2—Regeneration

The PBD6 tobacco (source SEITA France) is regenerated from foliar explants on a Murashige and Skoog (MS) basal medium comprising 30 g/l of sucrose as well as 200 µg/ml of kanamycin. The foliar explants are removed from plants cultivated in a greenhouse or in vitro and transformed according to the foliar disc technique (Horsh et al., 1985) in three successive stages: the first comprises the induction of shoots on a medium supplemented with 30 g/l of sucrose containing 0.05 mg/l of naphthyl acetic acid (NAA) and 2 mg/l of benzylaminopurine (BAP) for 15 days. The shoots formed during this stage are then developed for 10 days by cultivating on an MS medium supplemented with 30 g/l of sucrose but not containing any hormone. Developed shoots are then removed and they are cultivated on an MS rooting medium containing half of the content of salts, vitamins and sugar and not containing any hormone. After about 15 days, the rooted shoots are transferred into the soil.

2.3—Tolerance to Bromoxynil

Twenty transformed plants were regenerated and transferred into a greenhouse for each construct pRPA-RD-192 and pRPA-RD-193. These plants were treated in a greenhouse at the 5-leaf stage with an aqueous Pardner suspension corresponding to 0.2 kg of bromoxynil active ingredient per hectare.

All the plants showing complete tolerance to bromoxynil are used in the following experiments to test the effects of the expression of drosomycin on the tolerance of the transformed plants to fungal attacks.

EXAMPLE 3

Detection of Drosomycin in Transformed Tobaccos

An immunoblot analysis (as described by Coligan et al.) is used to detect the drosomycin produced by the transformed tobaccos, using a rabbit antibody directed against synthetic drosomycin attached to a KLH carrier protein, with the synthetic drosomycin as antigen.

The leaf proteins are extracted, first by grinding the frozen tissues at −180° C., followed by the addition of an extraction buffer (8 M urea, 50 mM Tris-HCl pH 6.8, 2% SDS, 5% β-mercaptoethanol, 10% sucrose, 2 mM EDTA and 10 mM dithiothreitol). The total quantity of extractable proteins is then measured. 100 µg of extracted proteins are then loaded into SDS-PAGE gel (20% acrylamide) wells for an immunoblot analysis (according to Coligan et al.).

For the plants transformed with the plasmid pRPA-RD-193 (drosomycin pre-pro), up to 160 ng of drosomycin were found per 100 µg of total proteins extracted from the leaves.

For the plants transformed with the plasmid pRPA-RD-192 (mature drosomycin), up to 50 ng of drosomycin were found per 100 µg of total proteins extracted from the leaves.

The drosomycin synthesized and isolated from the plants transformed with the plasmids pRPA-RD-192 and pRPA-RD-193 comigrates with the drosomycin isolated from drosophila. This result show that each of the drosomycins directed either towards the cytoplasm (pRPA-RD-192) or towards the extracellular matrix (pRPA-RD-193) leads to a mature drosomycin. In addition, the gel system used in this analysis (20% acrylamide) would have made it possible to easily detect drosomycin which would not have been transformed since the two constructs (ubiquitin-drosomycin and drosomycin pre-pro) are approximately 10 kD, against 5 kD for the mature drosomycin.

EXAMPLE 4

Resistance of the Transformed Tobaccos to *Botrytis cinerea*

15/20 plants derived from the plants obtained in Example 2.3 are cultivated in a greenhouse in transplanting pots of side 7 cm under the following conditions:

temperature: 16° C. at night; 19° C. during the day;
photoperiod: 14 h of darkness; 10 h of daylight;

hygrometry: 90-1400

Two leaves per plant are inoculated with 6 discs 6 mm in diameter per leaf, each disc consisting of a *Botrytis cinerea* suspension (100,000 spores/ml). The development of the infection is observed 7 days after the inoculation by measuring the increase in the diameter of each disc.

For most of the plants transformed with the plasmid pRPA-RD-192 (mature protein in the cytoplasm) or with the plasmid pRPA-RD-193 (extracellular drosomycin), no increase in the diameters of the discs or a very small increase, is observed, which indicates a high resistance to the infections caused by *Botritis cinerea*.

EXAMPLE 5

Resistance of Transformed Tobaccos to *Chalara elegans*.

The preceding procedure is repeated with the following operating conditions:

temperature: 18° C. at night; 22° C. during the day;

photoperiod: 14 h of darkness; 10 h of daylight.

The inoculation is carried out 18 days after sowing by supplying to each pot 1 ml of a suspension of endoconidia containing 1,000,000 conidia/ml. The infection results are read 21 days after the inoculation by observing the roots of plantlets previously cleaned with water. The development of the disease is assessed on a marking scale from 0 to 11, 0 corresponding to an absence of infection. For the plants transformed with the plasmid pRPA-RD-192 (mature protein in the cytoplasm) and those transformed with the plasinid pRPA-RD-193 (extracellular drosomycin), the mean notation is 4, which corresponds to a high resistance to *Chalara elegans*.

The results obtained in vivo in Examples 4 and 5 show that the transformation with the chimeric gene according to the invention confers on the transformed plant new fungus resistance properties, an activity [lacuna] is linked to preservation of the antifungal properties of the drosomycin produced by the transformed plants according to the invention.

REFERENCES

Ausubel, F. A. et al. (eds. Greene). Current Protocols in Molecular Biology. Publ. Wiley & Sons.
Bevan, M. et al. (1983). Nuc. Acids Res. 11: 369–385.
Brederode, F. T. M. et al. (1980). Nuc. Acids Res. 8: 2213–2223.
Callis et al. (1993). Plant Mol. Biol. 21: 895–906.
Carrington and Freed (1990). J. Virol. 64: 1590–1597.
Coligan, J. E. et al. (ed. V. B. Chanda). Current Protocols in Protein Science. Publ. Wiley & Sons.
Fehlbaum et al. (1994). J. Biol. Chem. 269: 331459–33163.
Horsch et al. (1985). Science 227: 1229–1231.
Jefferson et al. (1987). EMBO J. 6: 3901–3907.
Komari et al. (1986). J. Bacteriol. 166: 88–94.
Rothstein et al. (1981). Cold Spring Harb. Symp. Quant. Biol. 45: 99–105.
Stalker et al. (1988). J. Biol. Chem. 263: 6310–6314.
Odell, J. T. et al. (1985). Nature 313: 810–812.

What is claimed is:

1. A chimeric gene comprising:
  (a) a coding sequence encoding *Drosophila drosomycin* comprising a peptide sequence selected from SEQ ID NO:2 or SEQ ID NO:4 and
  (b) heterologous regulatory elements at positions 5' and 3' of said coding sequence that function in a plant.

2. A chimeric gene according to claim 1, wherein the coding comprises SEQ ID NO:1 or SEQ ID NO:3.

3. A chimeric gene according to claim 1, further comprising at least one herbicide tolerance gene.

4. A chimeric gene according to claim 1, further comprising at least one additional coding sequence encoding a peptide that confers resistance to diseases of fungal origin to the plant.

5. A chimeric gene according to claim 1, wherein the regulatory elements are selected from the group consisting of promoter sequences, terminator sequences, sequences that encode transit peptides, and any combination thereof.

6. A chimeric gene according to claim 5, wherein the promoter sequences are of bacterial, viral or plant origin.

7. A chimeric gene according to claim 6, wherein the regulatory promoter sequences are selected from the group consisting of promoter sequences of ribulose-biphosphate carboxylase/oxygenase (RuBisCo) small subunit genes and promoter sequences of the cauliflower mosaic virus (CaMV 19S or 35S).

8. A chimeric gene according to claim 6, wherein the promoter sequences are selected from the group consisting of histone promoters and actin promoters.

9. A vector for transforming plants, comprising at least one chimeric gene according to claim 1.

10. A transformed plant cell containing at least one chimeric gene according to claim 1.

11. A fungal disease resistant plant comprising the transformed cell according to claim 10, wherein said cell confers fungal resistance to said plant.

12. The fungal disease resistant plant of claim 10, wherein said plant is obtained by regeneration from the transformed cell.

13. A transgenic fungal resistant plant produced by the cultivation of the plant of claim 11 or 12.

14. A transgenic fungal disease resistant plant produced by crossing of the plant of claim 11 or 12.

15. A transgenic seed from a plant according to claims 11 or 12.

16. A method of producing transformed plants with increased resistance to fungal disease comprising:
  (a) transferring a chimeric gene according to claim 1 into plant cells; and
  (b) regenerating plants from the plant cells, wherein the chimeric gene confers increased resistance to fungal diseases in said transformed plants in comparison to an untransformed plant.

17. The method of claim 16 wherein the transferring is mediated by a bacterium selected from the group consisting of *Agrobacterium tumefaciens* and *Agrobacterium rhizogenes*.

18. The method of claim 16, wherein the transferring is by bombardment of the plant cells with particles coated with the chimeric gene.

19. The method of claim 16 further comprising transferring at least one herbicide tolerance gene into said plant cells.

20. The method of claim 16, further comprising transferring at least one additional chimeric gene into plant cells, wherein the transfer confers increased resistance to additional fungal diseases in said transformed plant.

21. A method of cultivating the plants according to one of claims 11 or 12 comprising (a) planting seeds of the plants in an area of a field appropriate for cultivation of the plants, (b) applying to the area of the field an agrochemical composition to produce cultivated plants, and (c) harvesting the cultivated plants when they reach a desired maturity to produce harvested cultivated plants.

22. The method of claim 21 wherein the agrochemical composition comprises at least one active product having at least one fungicidal and/or bactericidal activity.

23. The method of claim 22 wherein the active product exhibits activity complementary to that of drosomycin, wherein the active product has fungicidal and/or bactericidal activity against diseases which are insensitive to drosomycin or has fungicidal and/or bactericidal activity against diseases that are partially insensitive to drosomycin.

24. The method of claim 21 wherein the cultivated plants comprise seeds and wherein the method further comprises separating the seeds from the harvested cultivated plants to produce harvested cultivated seeds.

25. The method of claim 24 wherein the agrochemical composition comprises at least one active product having at least one fungicidal and/or bactericidal activity.

26. The method of claim 25 wherein the active product exhibits activity complementary to that of drosomycin, wherein the active product has fungicidal and/or bactericidal activity against diseases which are insensitive to drosomycin or has fungicidal and/or bactericidal activity against diseases that are partially insensitive to drosomycin.

\* \* \* \* \*

UNITED STATES PATENT AND TRADEMARK OFFICE
CERTIFICATE OF CORRECTION

PATENT NO. : 6,465,719 B1
DATED : October 15, 2002
INVENTOR(S) : DeRose et al.

It is certified that error appears in the above-identified patent and that said Letters Patent is hereby corrected as shown below:

<u>Title page,</u>
Item [73], Assignee, please replace the term "Cropscience" with the term
-- CropScience --
Item [75], Inventor(s), please replace the term "Lyons" with the term -- Lyon --

<u>Column 1,</u>
Line 12, please replace the term "Application" with the term
-- Applications --
Line 28, please replace the term "defence" with the term -- defense --

<u>Column 4,</u>
Line 36, the term "d" should be deleted
Line 38, please replace the term "arosomycin" with the term -- drosomycin --

<u>Column 5,</u>
Line 5, please replace the term "or" with the term -- and --
Line 21, please replace the term "Plan t cell" with the term -- Plant ell. --
Line 46, please replace the term "CAMV" with the term -- CaMV --

<u>Column 6,</u>
Line 60, please replace the term "selectable." with the term -- selectable --

<u>Column 7,</u>
Line 19, please replace the term "drosomycini," with the term -- drosomycin, --
Line 20, please replace the term "encodina" with the term -- encoding --
Line 22, please replace the term "zinally" with the term -- finally --

<u>Column 10,</u>
Line 20, please replace the term "*SaII*" with the term -- *SalI* --
Line 59, please replace the term "tumefaclens" with the term -- tumefaciens --

<u>Column 11,</u>
Line 24, please replace the term "Agrobacterium tumefaciens" with the term
-- *Agrobacterium tumefaciens* --

UNITED STATES PATENT AND TRADEMARK OFFICE
CERTIFICATE OF CORRECTION

PATENT NO. : 6,465,719 B1
DATED : October 15, 2002
INVENTOR(S) : DeRose et al.

It is certified that error appears in the above-identified patent and that said Letters Patent is hereby corrected as shown below:

Column 13,
Line 12, please replace the term "*Botritis*" with the term -- *Botrytis* --

Column 14,
Line 1, please replace the term "plasinid" with the term -- plasmid --
Line 7, please replace the term "[lacuna]" with the term -- that --

Column 23,
Line 50, please replace the term "claim 10," with the term -- claim 11, --

Signed and Sealed this

Thirteenth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,465,719 B1
DATED : October 15, 2002
INVENTOR(S) : DeRose et al.

It is certified that error appears in the above-identified patent and that said Letters Patent is hereby corrected as shown below:

<u>Title page,</u>
Item [73], Assignee, please replace the term "Cropscience" with the term
-- CropScience --.
Item [75], Inventors, please replace the term "Lyons" with the term -- Lyon --.

<u>Column 1,</u>
Line 12, please replace the term "Application" with the term -- Applications --.
Line 28, please replace the term "defence" with the term -- defense --.

<u>Column 4,</u>
Line 36, the term "d" should be deleted.
Line 38, please replace the term "arosomycin" with the term -- drosomycin --.

<u>Column 5,</u>
Line 5, please replace the term "or" with the term -- and --.
Line 21, please replace the term "Plan t cell" with the term -- Plant cell --.
Line 46, please replace the term "CAMV" with the term -- CaMV --.

<u>Column 6,</u>
Line 60, please replace the term "selectable." with the term -- selectable --.

<u>Column 7,</u>
Line 19, please replace the term "drosomycini," with the term -- drosomycin, --.
Line 20, please replace the term "encodina" with the term -- encoding --.
Line 22, please replace the term "zinally" with the term -- finally --.

<u>Column 10,</u>
Line 20, please replace the term "*SaII*" with the term -- *SalI* --.
Line 59, please replace the term "tumefaclens" with the term -- tumefaciens --.

<u>Column 11,</u>
Line 24, please replace the term "Agrobacterium tumefaciens" with the term
-- *Agrobacterium tumefaciens* --.

<u>Column 13,</u>
Line 12, please replace the term "*Botritis*" with the term -- *Botrytis* --.

<u>Column 14,</u>
Line 1, please replace the term "plasinid" with the term -- plasmid --.
Line 7, please replace the term "[lacuna]" with the term -- that --.

UNITED STATES PATENT AND TRADEMARK OFFICE
CERTIFICATE OF CORRECTION

PATENT NO.    : 6,465,719 B1
DATED         : October 15, 2002
INVENTOR(S)   : DeRose et al.

It is certified that error appears in the above-identified patent and that said Letters Patent is hereby corrected as shown below:

Column 23,
Line 50, please replace the term "claim 10," with the term -- claim 11, --.

This certificate supersedes Certificate of Correction issued May 13, 2003.

Signed and Sealed this

Twenty-fifth Day of October, 2005

JON W. DUDAS
*Director of the United States Patent and Trademark Office*